(12) United States Patent
Gharibans et al.

(10) Patent No.: US 11,712,566 B2
(45) Date of Patent: Aug. 1, 2023

(54) SACRAL NERVE STIMULATION

(71) Applicant: Alimetry Limited, Auckland (NZ)

(72) Inventors: Armen Gharibans, Auckland (NZ);
Gregory Brian O'Grady, Auckland (NZ); Peng Du, Auckland (NZ);
Jonathan Christopher Erickson, Lexington, VA (US)

(73) Assignee: Alimetry Limited, Auckland (NZ)

( * ) Notice: Subject to any disclaimer, the term of this patent is extended or adjusted under 35 U.S.C. 154(b) by 181 days.

(21) Appl. No.: 16/991,166

(22) Filed: Aug. 12, 2020

(65) Prior Publication Data

US 2021/0046317 A1 Feb. 18, 2021

(30) Foreign Application Priority Data

Aug. 12, 2019 (NZ) ..................... 756240

(51) Int. Cl.
| | |
|---|---|
| *A61N 1/36* | (2006.01) |
| *A61N 1/05* | (2006.01) |
| *A61B 5/00* | (2006.01) |
| *A61B 5/392* | (2021.01) |

(52) U.S. Cl.
CPC .......... *A61N 1/36139* (2013.01); *A61B 5/392* (2021.01); *A61B 5/4836* (2013.01); *A61B 5/6823* (2013.01); *A61B 5/6833* (2013.01); *A61N 1/0551* (2013.01); *A61N 1/36062* (2017.08); *A61N 1/36153* (2013.01);
(Continued)

(58) Field of Classification Search
CPC . A61B 2562/046; A61B 5/392; A61B 5/4836; A61B 5/6823; A61B 5/6833; A61N 1/0456; A61N 1/0484; A61N 1/0551; A61N 1/323; A61N 1/36007; A61N 1/36031; A61N 1/36062; A61N 1/36139; A61N 1/36153; A61N 1/36171; A61N 1/36175
See application file for complete search history.

(56) References Cited

U.S. PATENT DOCUMENTS

| | | | |
|---|---|---|---|
| 5,109,870 | A | 5/1992 | Silny et al. |
| 5,471,982 | A | 12/1995 | Edwards et al. |
| 5,551,425 | A | 9/1996 | Essen-Moller |

(Continued)

FOREIGN PATENT DOCUMENTS

WO   2017201538 A1   11/2017

OTHER PUBLICATIONS

V. Patton et al., "The effect of sacral nerve stimulation on distal colonic motility in patients with faecal incontinence," British Journal of Surgery Mar. 2013, pp. 959-968, vol. 100.
(Continued)

*Primary Examiner* — George Manuel
(74) *Attorney, Agent, or Firm* — Pilloff Passino & Cosenza LLP; Martin J. Cosenza

(57) ABSTRACT

A method including transcutaneously measuring motility patterns, in the colon of a recipient of an implantable neuromodulator, responsive to an electrical stimulus delivered by the implantable neuromodulator, and programming the implantable neuromodulator responsive to the measured motility patterns, wherein the method comprises adjusting at least one parameter of the implantable neuromodulator that defines the electrical stimulus that the implantable neuromodulator is configured to deliver to the recipient.

20 Claims, 11 Drawing Sheets

(52) U.S. Cl.
CPC ..... *A61N 1/36171* (2013.01); *A61N 1/36175* (2013.01); *A61B 2562/046* (2013.01)

(56) References Cited

U.S. PATENT DOCUMENTS

| | | | |
|---|---|---|---|
| 6,006,755 | A | 12/1999 | Edwards |
| 6,053,913 | A | 4/2000 | Tu et al. |
| 6,236,883 | B1 | 5/2001 | Ciaccio et al. |
| 6,351,665 | B1 | 2/2002 | Koch |
| 6,389,311 | B1 | 5/2002 | Whayne et al. |
| 6,430,426 | B2 | 8/2002 | Avitall |
| 6,480,747 | B2 | 11/2002 | Schmidt |
| 6,529,756 | B1 | 3/2003 | Phan et al. |
| 6,611,627 | B1 | 8/2003 | LaRossa et al. |
| 6,741,878 | B2 | 5/2004 | Fuimaono et al. |
| 6,745,062 | B1 | 6/2004 | Finneran et al. |
| 7,177,703 | B2 | 2/2007 | Boveja et al. |
| 7,291,146 | B2 | 11/2007 | Steinke et al. |
| 8,190,262 | B2 | 5/2012 | Gerber et al. |
| 9,789,308 | B2 | 10/2017 | Southwell et al. |
| 10,092,762 | B2 | 10/2018 | Jiang et al. |
| 2002/0065455 | A1 | 5/2002 | Ben-Haim et al. |
| 2002/0065515 | A1 | 5/2002 | Falwell et al. |
| 2003/0114770 | A1 | 6/2003 | Koch |
| 2003/0144708 | A1 | 7/2003 | Starkebaum |
| 2005/0222638 | A1 | 10/2005 | Foley et al. |
| 2006/0058598 | A1 | 3/2006 | Esposito |
| 2006/0066911 | A1 | 3/2006 | Miller et al. |
| 2006/0074456 | A1* | 4/2006 | Pyles ............... A61N 1/36007 607/40 |
| 2006/0122660 | A1 | 6/2006 | Boveja et al. |
| 2007/0299352 | A1 | 12/2007 | Harlev et al. |
| 2008/0027358 | A1 | 1/2008 | Gregersen et al. |
| 2008/0228060 | A1 | 9/2008 | Tegg |
| 2013/0035576 | A1 | 2/2013 | O'Grady et al. |
| 2017/0182318 | A1 | 6/2017 | Fisher et al. |
| 2018/0056063 | A1 | 3/2018 | Farajidavar et al. |

OTHER PUBLICATIONS

Advisory action received for U.S. Appl. No. 13/880,041 (dated Oct. 3, 2017, 3 pages).
Tara Der et al., "Interstitial Cells of Cajal and Inflammation-Induced Motor Dysfunction in the Mouse Small Intestine," Gastroenterology, Dec. 2000, pp. 1590-1599, vol. 119, No. 6.
Peng Du et al., "High-Resolution Mapping of In Vivo Gastrointestinal Slow Wave Activity Using Flexible Printed Circuit Board Electrodes: Methodology and Validation," Annals of Biomedical Engineering, Apr. 2009, 16 pages, vol. 37, No. 4.
J. U. Egbuji et al., "Origin, Propagation and Regional Characteristics of Porcine Gastric Slow Wave Activity Determined by High-Resolution Mapping", Neurogastroenterology and Motility, Oct. 2010, vol. 22, No. 10.
Final Office Action received for U.S. Appl. No. 13/880,041 (dated Feb. 19, 2016, 23 pages).
Final Office Action received for U.S. Appl. No. 13/391,621 (dated Jan. 26, 2017, 25 pages).
Final Office Action received for U.S. Appl. No. 13/880,041 (dated Jul. 31, 2017, 13 pages).
International Preliminary Report on Patentability received for PCT patent application PCT/NZ2010/000164 (completed on Jan. 19, 2012, 7 pages).
International Search Report and Written Opinion received for PCT patent application PCT/NZ2010/000164 (dated Dec. 21, 2010, 17 pages).
International Preliminary Report on Patentability received for PCT patent application PCT/NZ2011/000217 (dated Apr. 23, 2013, 5 pages).
International Search Report and Written Opinion received for PCT patent application PCT/NZ2011/000217 (dated Jun. 1, 2012, 8 pages).
Zhiyue Lin et al., "Gastric myoelectrical activity and gastric emptying in patients with functional dyspepsia", The American Journal of Gastroenterology, Sep. 1999, pp. 2,384-2,389, vol. 94, No. 9.
Non-Final Office Action received for U.S. Appl. No. 13/880,041 (dated Nov. 17, 2017, 13 pages).
Non-Final Office Action received for U.S. Appl. No. 13/391,621 (dated Apr. 28, 2016, 18 pages).
Non-Final Office Action received for U.S. Appl. No. 13/880,041 (dated Feb. 8, 2017, 12 pages).
Non-Final Office Action received for U.S. Appl. No. 13/880,041 (dated May 18, 2015, 15 pages).
Gregory O'Grady et al., "Origin and Propagation of Human Gastric Slow-Wave Activity Defined by High-Resolution Mapping", Am. J. Physiol. Gastrointest. Liver Physiol, Sep. 2010, pp G585-G592, vol. 299.
Restriction Election Requirement received for U.S. Appl. No. 13/391,621 (dated Oct. 6, 2015, 9 pages).
Jiri Silny, "Intraluminal Multiple Electric Impedance Procedure for Measurement of Gastrointestinal Motility", Journal of Gastrointestinal Motility, Sep. 1991, pp. 151-162, vol. 3, No. 3.
Sitabhra Sinha et al., "Critical role of inhomogeneities in pacing termination of cardiac re-entry", Chaos: An Interdisciplinary Journal of Nonlinear Science, Sep. 2002, pp. 893-902, vol. 12, No. 3.
Gary Tse et al., "Electrophysiological Mechanisms of Gastrointestinal Arrhythmogenesis: Lessons from the Heart," Frontiers in Physiology, Jun. 2016, vol. 7, Article 230.

* cited by examiner

SACRAL NERVE STIMULATION

CROSS-REFERENCE TO RELATED APPLICATIONS

This application claims the benefit of New Zealand Application No. 756240 filed on Aug. 12, 2019, the entire disclosure of which is incorporated herein by reference.

BACKGROUND

Functional disorders of the colon, including irritable bowel syndrome, affect an estimated >10% of the population worldwide. The highest prevalence is in the United States and Europe. Symptoms of abdominal pain and altered bowel habits can be debilitating and result in a profound negative impact on quality of life.

Faecal incontinence is a common disorder with a prevalence that rises with age.

Individuals suffering from faecal incontinence find it distressing and socially incapacitating. The prevalence in adults, with at least monthly episodes of incontinence, is estimated to be >10%. It has been shown that between four and six percent of women having a vaginal delivery will suffer from faecal incontinence.

Dietary manipulation, pharmacological drugs, pelvic floor physiotherapy as well as surgery are often used as combination treatment for patients suffering from faecal incontinence. A stoma (colostomy or ileostomy) is reserved for patients with end-stage faecal incontinence where available treatments have failed or are inappropriate due to comorbidities. While a stoma is successful in controlling faecal incontinence, it is associated with significant psychosocial and economic issues and stoma-related complications. Sacral nerve stimulation (SNS) is an innovative treatment for end-stage faecal incontinence and could obviate the need for a stoma.

SUMMARY

In a first embodiment, a method for adjusting an implantable sacral nerve stimulator is disclosed. The method comprises measuring motility patterns, in the colon of a recipient of an implantable neuromodulator, responsive to an electrical stimulus delivered by the implantable neuromodulator, and programming the implantable neuromodulator responsive to the measured motility patterns, wherein the method comprises adjusting at least one parameter of the implantable neuromodulator that defines the electrical stimulus that the implantable neuromodulator is configured to deliver to the recipient.

According to a further aspect the method comprises setting the charge that the implantable neuromodulator is configured to deliver to stimulate the sacral nerve or spinal cord of the recipient responsive to the measured colon motility patterns.

According to a further aspect the method comprises setting a compliance voltage for the implantable neuromodulator responsive to the measured colon motility patterns.

According to a further aspect the method comprises setting at least one of a pulse width, a pulse amplitude, or a pulse frequency for the electrical stimulus that the implantable neuromodulator is configured to deliver to the recipient.

According to a further aspect the method comprises the implantable neuromodulator stimulating the spinal cord or sacral nerve of the recipient, with an electrical stimulus defined by the at least one adjusted parameter, and measuring the motility patterns, in the colon of the recipient, responsive to the electrical stimulus.

According to a further aspect the method comprises adjusting the at least one parameter of the electrical stimulus that the implantable neuromodulator is configured to deliver to the recipient until the measured motility patterns are indicative of rhythmic retrograde motor events occurring at about 2 to about 6 cycles per minute in the rectosigmoid.

According to a further aspect the method comprises adjusting the at least one parameter of the electrical stimulus that the implantable neuromodulator is configured to deliver to the recipient until the measured motility patterns are indicative of a rectosigmoid brake or cyclic motor pattern in the lower descending colon and/or in the rectosigmoid following ingestion of a meal.

According to a further aspect the method comprises transcutaneously measuring the response of smooth muscle in the colon to electrical stimulation of the spinal cord or the sacral nerve.

According to a further aspect the method comprises transcutaneously measuring the electrical activity of the recipient's colon, and resolving the electrical activity into electrical waves that are indicative of colonic motility, wherein each electrical wave represents a propagating contraction of smooth muscle within the colon.

According to a further aspect the method comprises spatially mapping the propagation of the electrical waves along the recipient's colon responsive to electrical stimulation of the spinal cord or sacral nerve.

According to a further aspect the method comprises performing transcutaneous electrocolonography concurrently with electrical stimulation of the spinal cord or sacral nerve.

In a further embodiment, a method of adapting electrical stimulation is disclosed. The method comprises transcutaneously measuring the smooth muscle response of the colon to electrical stimulation of the sacral nerve, and adapting the electrical stimulation responsive to the measured smooth muscle response.

According to a further aspect the invention broadly comprises a method of transcutaneously measuring a smooth muscle response, in the colon of a patient, to electrical stimulation of the spinal cord or the sacral nerve, and adapting at least one characteristic of the electrical stimulation delivered to the spinal cord or the sacral nerve responsive to the measured smooth muscle response.

According to a further aspect the method comprises transcutaneously measuring electrical activity of the patient's colon, and resolving the electrical activity into electrical waves that are indicative of colonic motility, wherein each electrical wave represents a propagating contraction of smooth muscle within the colon.

According to a further aspect the method comprises identifying colonic dysmotility from the propagating electrical waves, and adjusting the charge delivered to the spinal cord of the sacral nerve to treat the identified dysmotility.

According to a further aspect the method comprises progressively increasing the current delivered to the spinal cord or sacral nerve of the patient to induce retrograde propagating sequences in the colon.

According to a further aspect the method comprises progressively reducing the current delivered to the patient until the smooth muscle response of the colon is indicative of a colonic motility disorder.

In a further embodiment, a method of delivering electrical stimulation to a patient to treat a colonic motility disorder is disclosed. The method comprises measuring propagating electrical activity in the colon of the patient, responsive to electrical stimulation, with an electrode matrix positioned on the abdomen of the patient, and modifying the electrical stimulation delivered to the patient in order to evoke an altered motility pattern in the colon.

According to a further aspect the method comprises centering the electrode matrix over a section of the abdomen between the left iliac crest and the midline of the patient.

According to a further aspect the method comprises centering the electrode matrix over a section of the abdomen between the umbilicus and an upper region of the symphysis pubis.

According to a further aspect the method comprises adhering the electrode matrix to the skin of the patient overlying a rectosigmoid segment of the colon.

According to a further aspect the method comprises measuring post meal activity in the lower descending colon and/or rectosigmoid, and modifying the electrical stimulation to produce a motility pattern that reduces the incidence of faecal incontinence.

According to a further aspect the method comprises modifying the electrical stimulation to produce a rectosigmoid brake or cyclic motor patterns.

BRIEF DESCRIPTION OF THE DRAWINGS

Embodiments are described with reference to the accompanying drawings, wherein.

DETAILED DESCRIPTION

Figure 1:
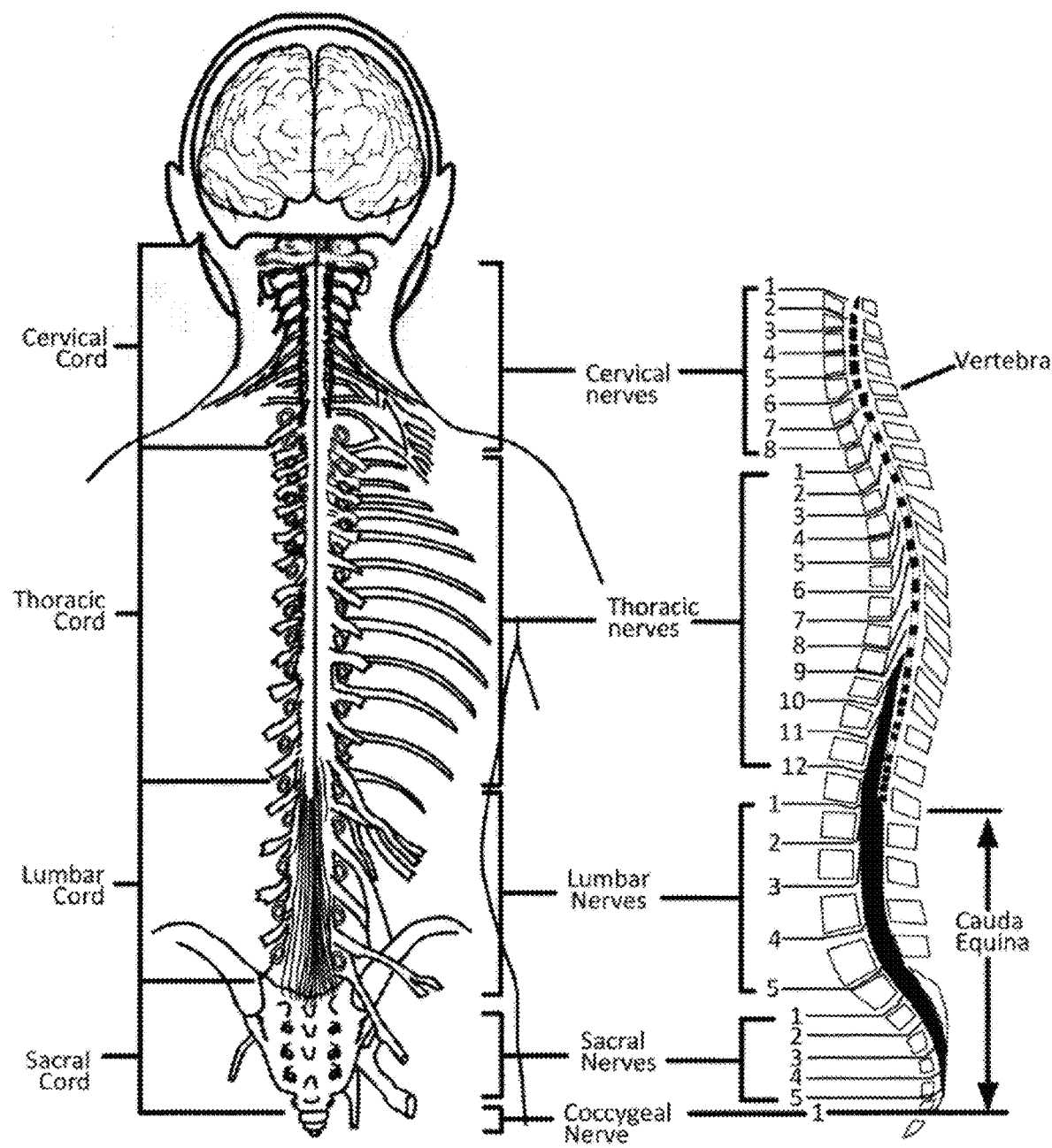
FIG. 1 is a schematic representation of a human spinal cord showing four regions of the spinal cord and some of the nerve structures.

A neurostimulator that is configured to provide electrical stimulation therapy to tissue in the sacral region is disclosed. Neurostimulation therapy in the sacral region can be used to alleviate symptoms associated with a variety of pelvic floor disorders, including faecal incontinence. For example, an implanted neurostimulator can apply electrical stimulation pulses to the sacral or pudendal nerves to provide improved bowel control. It is also possible to electrically stimulate the sacral and/or pudendal nerves transcutaneously with a transcutaneous neurostimulator.

Sacral nerve stimulation can be an effective treatment for faecal incontinence. In some embodiments, it involves delivery of electrical stimulation via an implantable electrode that is positioned next to a sacral nerve root. In other embodiments, it involves delivery of electrical stimulation via an implantable electrode that is positioned higher up the spinal cord (e.g. in the lumbar region). Sacral nerve stimulation achieves its effect through several physiological mechanisms. It stimulates the motor output from the sacral nerves and pudendal nerve, modulates the local spinal reflex arcs, and modulates the autonomic supply to the distal colon and rectum and pelvic floor as well as spinal tracts to the higher centre in the brain.

An implantable sacral nerve neurostimulator can include a stimulation pulse generator and one or more leads carrying electrodes for delivery of the stimulation pulses to nerve tissue. The neurostimulator operates according to a set of stimulation parameters that are stored in memory. The stimulation parameters are usually set by a clinician. An external programmer is used to communicate with implanted neurostimulators by wireless telemetry to set stimulation parameters such as pulse frequency, pulse width, pulse amplitude and pulse duration.

The neuromodulator can be programmed to evoke increased cyclic motor patterns (relative to a baseline without electrical stimulation). For example, electrocolonography measurements can be used to identify the onset and/or a change in rate of propagating motor patterns during neuromodulator programming. In at least some embodiments, the neuromodulator can be programmed to evoke propagating cyclic motor patterns in the range of 2 cycles per minute to 6 cycles per minute. The neuromodulator can be programmed to evoke and/or increase antegrade cyclic motor patterns, retrograde cyclic motor patterns, or a combination of antegrade and retrograde cyclic motor patterns.

Stimulation parameters are typically loaded into the neurostimulator or external monitor/programmer at a clinic. The parameters can be organized as one or more distinct programs that can be selected using the external monitor/programmer. Also, the external monitor/programmer can permit a patient to adjust one or more individual parameters. The parameters may be reprogrammed in a subsequent clinical visit if the results provided by existing parameters are unsatisfactory.

The neuromodulator applies electrical stimulation pulses to the nervous system of the recipient to treat disorders. Some of the nerve structures that extend along the human spinal cord are shown schematically in FIG. 1. The spinal cord is an elongate tubular structure that comprises nervous tissue. Four regions of the spinal cord are shown in FIG. 1: the cervical cord, the thoracic cord, the lumbar cord and the sacral cord. The nerve structures of the sacrum region are shown in greater detail in FIG. 2.

Figure 2:
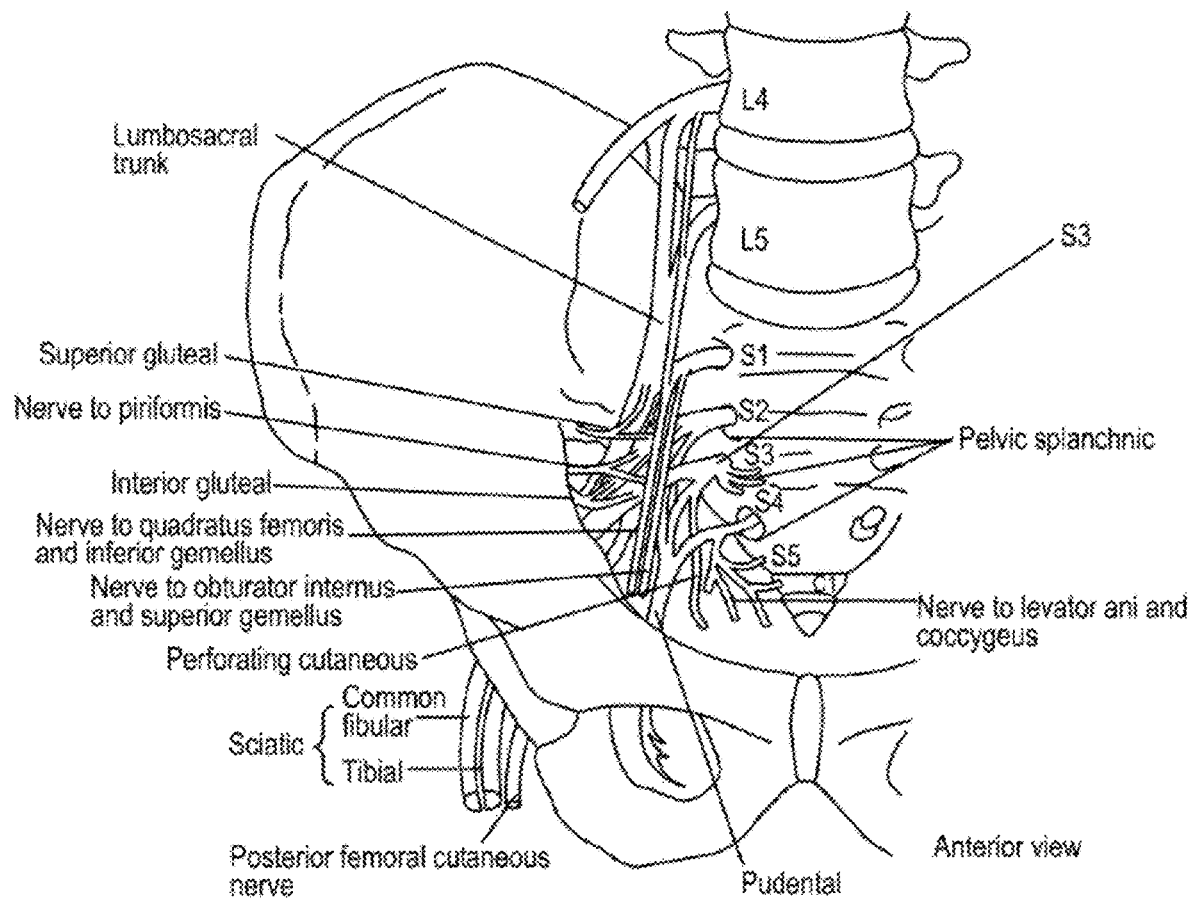
FIG. 2 is a schematic representation of the nerve structures in the sacrum region.

The brain and spinal cord together make up the central nervous system. Nervous tissue extends from the brainstem along the cervical cord, through the thoracic cord and to the space between the first and second lumbar vertebra in the lumbar cord. FIG. 2 shows nerve fibres exiting the spinal cord in the lumbar region. The nerve fibres are shown in bundles that travel through the sacral foramens of the sacrum.

The sacral nerve contains both afferent and efferent nerve fibres. These nerve fibres are responsible for part of the sensory perception and movements of the lower extremities of the human body. The branches of the sacral nerve transmit electrical impulses between the brain and the muscle/organs that are innervated by the sacral nerve. The electrical impulses convey sensory information to the central nervous system and/or motor control from the central nervous system.

Nerve cells can be excited by increasing the electrical charge within the neuron. This increases the membrane potential inside the cell with respect to the surrounding extracellular fluid. The threshold stimulus intensity needed for excitation occurs when the net inward current (largely determined by Sodium ions) is greater than the net outward current (largely carried by Potassium ions). For most neurons, the critical firing threshold stimulus is around −55 mV inside the nerve cell (relative to the extracellular fluid). When a nerve cell fires it causes an electrical impulse to pass along the axon in a cascading effect known as an action potential. This action potential is an "all or nothing" phenomenon that is triggered once the threshold stimulus intensity is reached. When the threshold is not reached, the graded depolarization will not generate an action potential and the signal will not propagate along the axon.

Prior to stimulation, the metabolic activity of the excitable cells (e.g. nerve and/or muscle cells) maintains an ionic gradients across the cell membrane. This produces a high concentration of potassium (K+) ions inside the cell and a high concentration of sodium (Na+) ions in the extracellular environment in a resting state. The net result of the ionic gradient is a transmembrane potential that is largely dependent on the potassium ion (K+) gradient. Typically in nerve cells, the resting membrane potential is slightly less than −70 mV, with the outside being positive with respect to inside. To stimulate an excitable cell, the transmembrane potential has to be reduced by a critical amount. When the threshold potential is reached, a regenerative process takes place: sodium ions enter the cell, potassium ions exit the cell, and the transmembrane potential falls to zero (depolarizes), reverses slightly, and then recovers or repolarizes to the resting membrane potential.

Pulsed electrical stimulation induces nerve impulses in the form of action potentials in the nerve fibres. A neurostimulator 5 that is configured to deliver electrical stimulation therapy to excitable tissue of a recipient is shown schematically in FIG. 3. The depicted neurostimulator 5 is an implantable sacral nerve stimulator that is implanted in the sacral region of a recipient. In some embodiments, the sacral nerve stimulator can be implanted in a different position within the spinal cord of a patient (e.g. in the lumbar region) while still targeting stimulation of the sacral nerve (usually with increased off-target effects). The illustrated neurostimulator 5 has a lead 7 that extends through the foramen of the sacrum. The lead 7 terminates in an electrode array 4 that is positioned adjacent the anterior sacral nerve root in FIG. 3. The electrode array 4 comprises a plurality of electrically conductive electrodes 2 that deliver electrical charge to the surrounding tissue. The electrodes 2 are embedded in a flexible carrier. For example, the electrode array 4 can comprises a plurality of platinum pads that are embedded in a silicone carrier. The size and/or shape of the electrodes 2 can be constrained by the intended application. For example, the cross section of the electrodes 2 shown in FIG. 3 cannot be larger than the sacral foramen that the electrode array 4 projects through.

Figure 3:
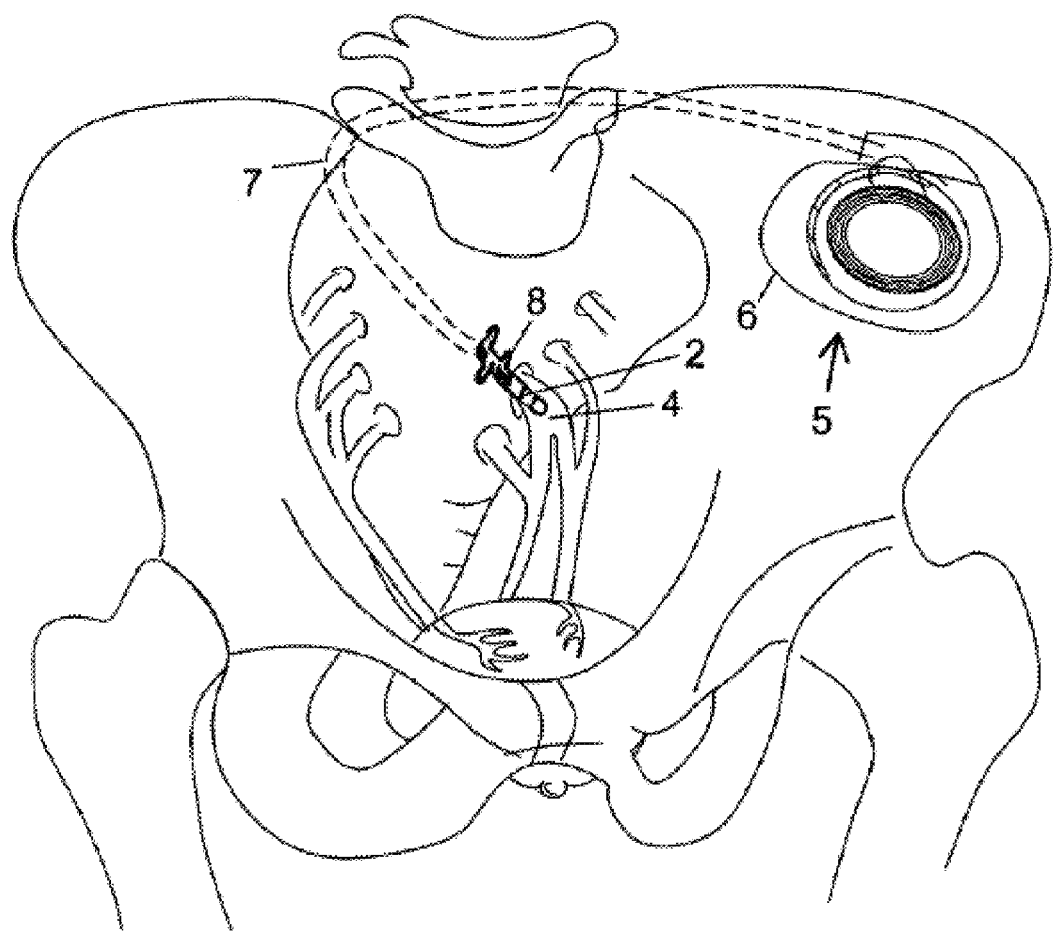
FIG. 3 is a schematic representation of the sacrum region showing the placement of the implanted sacral nerve stimulator lead in contact with the sacral nerve(s) or branches.

A stimulator unit 6 is shown implanted behind the left iliac crest in FIG. 3. The stimulator 6 houses the implant electronics. The housing of the stimulator 6 comprises a structural chassis and one or more feedthrough(s). The feedthrough(s) seal the chassis to form a hermetic enclosure for the implant electronics and electrically bridge the hermetic/non-hermetic sides of the stimulator 6. The chassis and the feedthrough(s) are both fabricated from biocompatible materials. For example, the chassis can be fabricated from titanium or ceramic, and the feedthrough(s) can be fabricated from ceramic or glass. In at least some embodiments, the stimulator housing is encapsulated with a smooth biocompatible coating (e.g. a silicone encapsulant) that resists biofilm formation.

The implant electronics can comprise a controller (such as an ASIC or microcontroller) that controls operation of the neuromodulator 5, at least one current source that supplies stimulation current, and a battery that powers the implant electronics. The implant electronics are typically mounted to a PCBA (printed circuit board assembly) that is secured within the hermetic enclosure of the stimulator 6. The PCBA can incorporate other component (such as ancillary controllers) that form part of the implant electronics package. For example, the PCBA can incorporate a telemetry circuit that facilitates communication with an external programmer and/or a charging circuit that recharges the implanted battery with power received transcutaneously from an external charger.

A stimulation controller (e.g. an ASIC or microcontroller) regulates the charge that the neuromodulator 5 injects into the tissue surrounding the electrodes 2. For example, the stimulation controller can control the amplitude and/or the duration of the electrical pulses applied to the electrodes 2 during stimulation. The stimulation controller switches the current source(s) to produce the stimulation pulses. For example, the stimulation controller can switch selected electrodes pairs (a source electrode and a sink electrode) into electrical connection with a single current source, and/or switch each of the selected electrodes into electrical connection with a dedicated current source (where the implant electronics comprises more than current source). Each implant current source is configured to supply a constant current when operating in compliance (i.e. when the current source is operating below the compliance voltage).

In some embodiments, the mode of stimulation used by the neuromodulator 5 can be programmed by a clinician. For example, the neuromodulator 5 can be configured to deliver charge balanced biphasic stimulation pulses or monophasic stimulation pulses (with adequate charge recovery after each pulse). The implant electronics can be programmed to control the rail voltage of the current source. In at least some embodiments, the implant electronics include a charge recovery circuit that prevents residual charge build-up in the tissue surrounding the stimulation electrodes 2. For example, the charge recovery circuit can comprise a bank of capacitors that electrically isolate the implant electronics from each of the electrodes 2. The discharge of the isolating capacitors when the stimulation current is removed passively recovers any residual charge remaining in the tissue.

The stimulator 6 is physically and electrically connected to the electrode array 4 by the lead 7. The lead 7 comprises a set of conductors that are encapsulated in a biocompatible carrier. The conductors convey electrical current from the feedthrough(s) to the electrodes 2 of the electrode array 4. The carrier electrically isolates each of the conductors and gives the lead 7 its mechanical properties (e.g. flexibility and resilience). For example, the lead 7 can comprise a set of platinum wires encapsulated in a silicone carrier. In some embodiments, the lead 7 includes an anchoring segment that is configured to hold the lead 7 in position following implantation. For example, the anchoring segment can comprise a series of tines 8 that extend radially outward from the lead 7 to prevent the lead migrating relative to the foramen. The tines 8 can be disposed dorsal and/or ventral of the sacral foramen through which the lead passes.

In some embodiments, the stimulator housing can incorporate one or more electrodes. For example, an electrode can be secured to the chassis of the stimulator 6 by an electrically isolating encapsulant (e.g. the silicone that encapsulates the stimulator 6 housing). The neuromodulator 5 can be configured to use the stimulator electrode for monopolar stimulation and/or electrophysiological measurement. In at least some embodiments, the stimulator electrode can have a significantly larger surface area than the lead electrodes 2. The greater surface area help to alleviate charge density restrictions for monopolar stimulation and/or increase the sensitivity of electrophysiological measurements obtained by the neurostimulator. For recipients with high stimulation thresholds, multiple lead electrodes 2 can be used in conjunction with a stimulator electrode to reduce the effective charge density needed for adequate stimulation.

Figure 4:
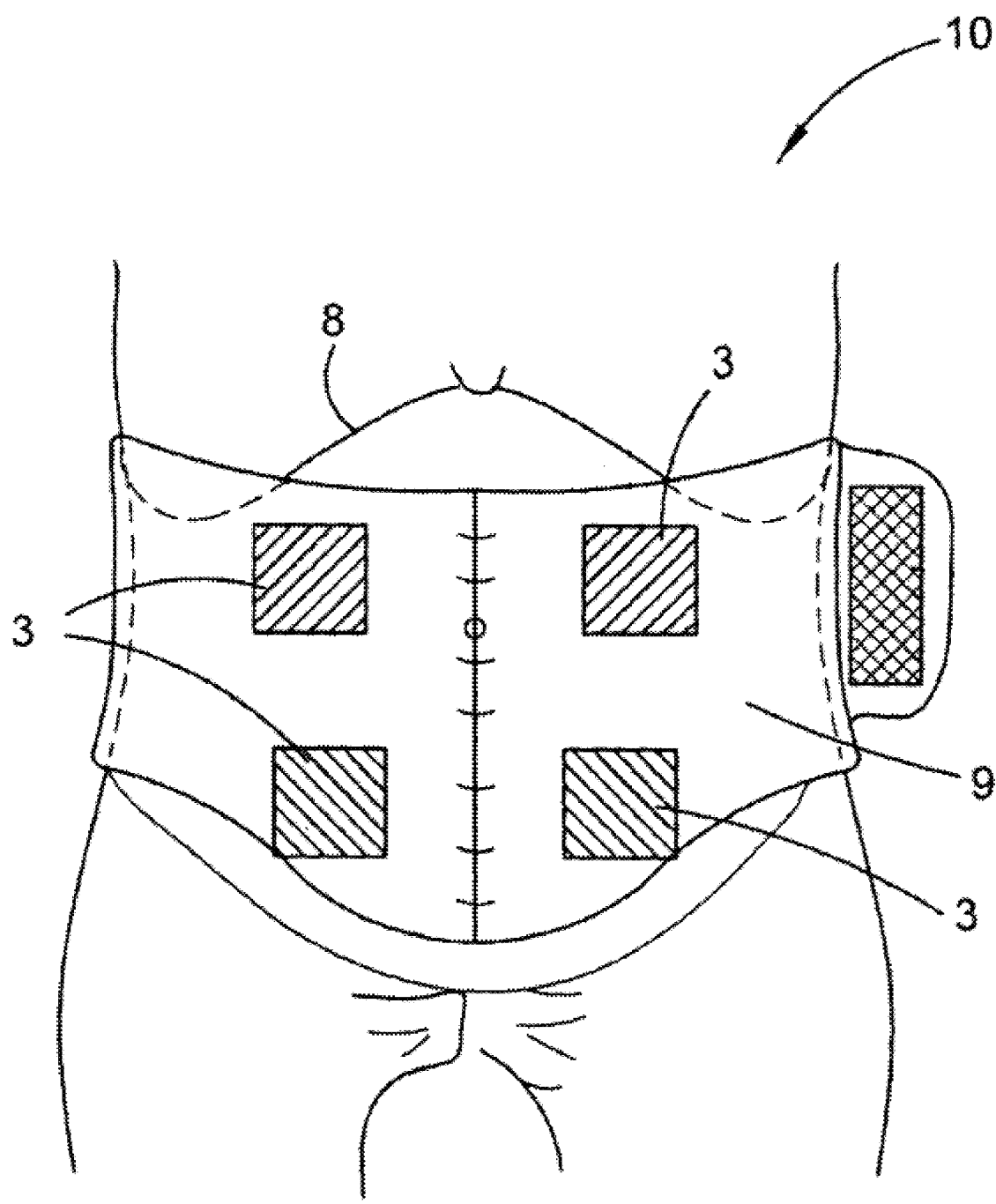
FIG. 4 is a schematic representation of a non-invasive sacral nerve stimulator secured about the lower torso of a recipient.

A transcutaneous sacral nerve stimulator 10 is shown schematically in FIG. 4. The stimulator 10 comprises electrode pairs that are positioned around the abdomen of the recipient adjacent the sacral region. The frontal electrodes 3 of the stimulator 10 are shown in FIG. 4. The electrodes 3 are supported by a belt 9 that is worn around the torso below the costal margin 8. The belt 9 and the electrodes 3 are in contact with the recipient's skin. In some embodiments, a conductive biocompatible adhesive can be applied to the electrodes 3 to ensure adequate electrical connection with the skin.

The sacral nerve stimulator 10 is controlled by stimulation electronics (not shown in FIG. 4). The stimulation electronics are configured to generate an oscillating electric field between each pair of electrodes 3. The electric fields combine in the sacral region to produce a stimulation current at the root of the sacral nerve. The electrodes 3 are connected to the stimulation electronics by electrical leads. The electrical leads conduct stimulation current from the stimulation electronics to the electrodes 3. The stimulator 10 shown in FIG. 4 has the electrical leads stitched into the fabric of the belt 9. The stimulation electronics can be secured to the belt 9, worn independently by the recipient (e.g. in a backpack or should sling), or form part of a home/hospital unit (e.g. a bedside stimulation controller).

Figure 5:
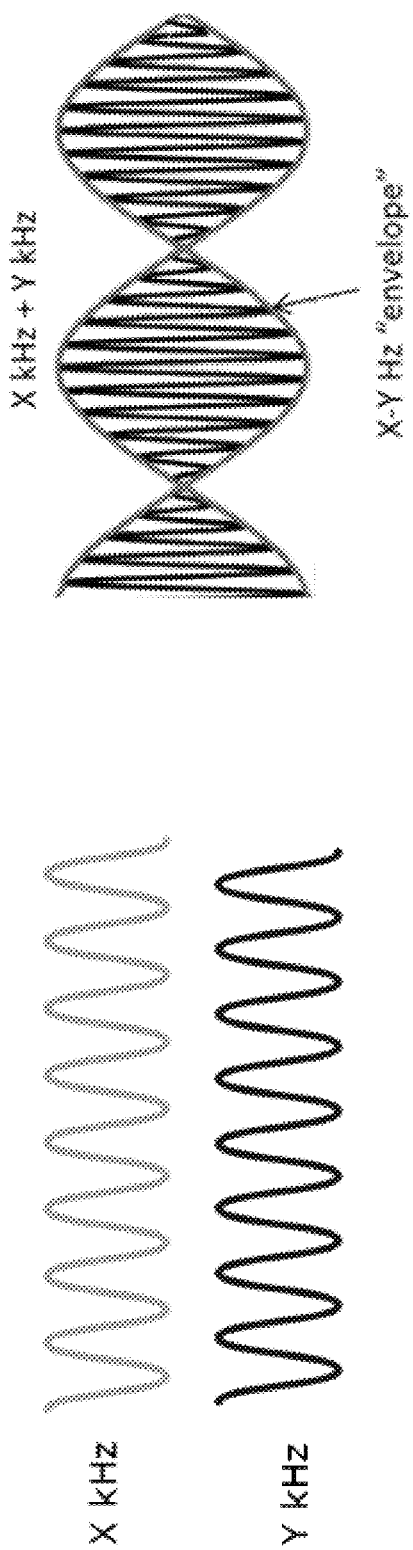
FIG. 5 is a diagram showing the combination electric fields for interferential stimulation.

An exemplary representation of interferential stimulation is shown schematically in FIG. 5. The illustrated embodiment comprises two high frequency electric fields that are generated between opposing electrodes 3 (e.g. a frontal electrode paired with a rear electrode) operating at differing carrier frequencies. The electric fields superimpose adjacent the sacral nerve roots to produce a stimulation field within the nominal frequency range for sacral nerve stimulation.

The frequency of each electric field is sufficiently high to facilitate adequate tissue penetration. The elevated frequency of each electric field also avoids unintended stimulation as the oscillations are above the intrinsic stimulation frequency for most forms of biological tissue in the sacral region (e.g. in excess of 1000 Hz). Both electric fields propagate through the abdomen between the respective electrode pairs. The placement of the electrodes 3 on the belt 9 of the stimulator 10 ensure that the electric fields combine adjacent the sacral nerve root.

The implant electronics drive each electrode pair at slightly different frequencies. For example, the stimulator 10 can be configured to generate a first electric field at 1000 Hz and a second electric field at 1050 Hz. The oscillating frequency of each electric field is selected to produce an interference pattern having a beat frequency within the nominal stimulation range for the sacral nerve (e.g. 50 Hz). The envelop frequency of the combined (superimposed) waveform is equivalent to the frequency difference between the high frequency component fields.

Some nerves innervate both organs and muscles. For example, the sacral nerve includes a branch that terminates at the descending colon and a branch that terminates at muscle in the leg/foot. Electrical stimulation of the sacral nerve at or near the nerve root can evoke a response in more than one nerve branch. The neuromuscular response in the lower extremities to electrical stimulation can be used to objectively verify stimulation of the sacral nerve (i.e. to confirm that the neurons of the sacral nerve are firing). For example, a physician can determine whether a targeted nerve is being stimulated by monitoring muscle response in the lower extremities (e.g. using electromyography/EMG measurements). High levels of stimulation can evoke a visible muscle response. Lower level stimulation can still produce adequate nerve activation for a targeted organ while evoking no corresponding muscle response, or a response only detectable with electromyography.

Figure 6:
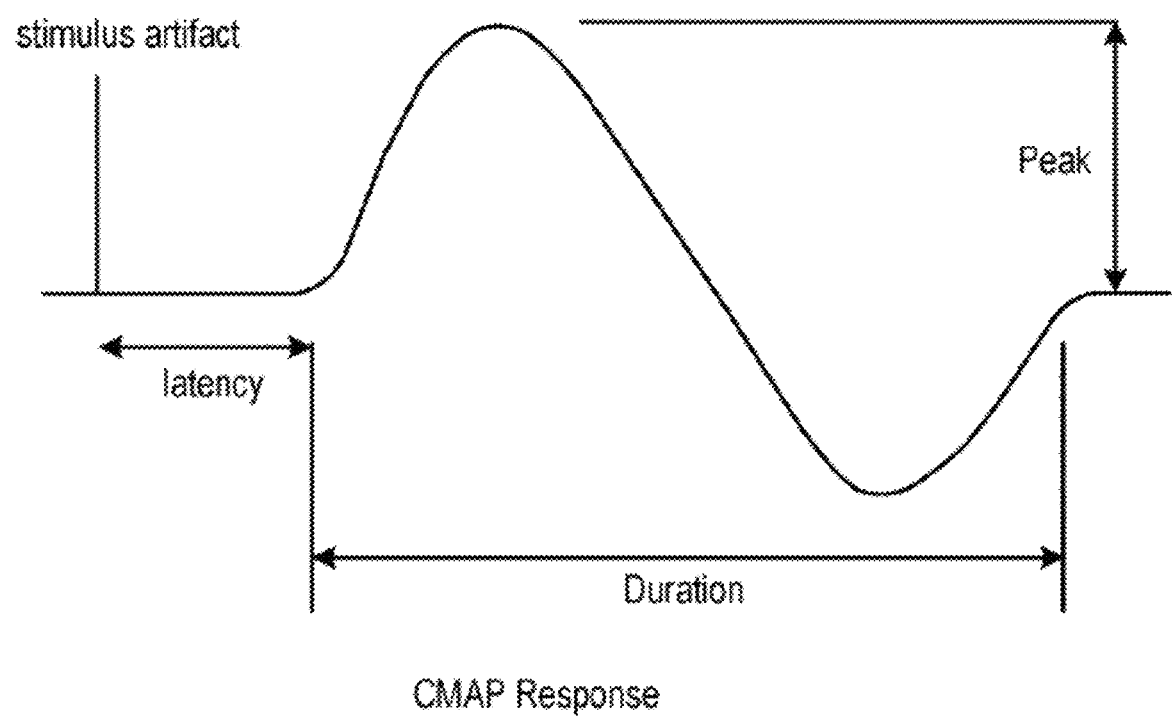
FIG. 6 is a schematic representation of an electromyography measurement depicting a compound muscle action potential response in the flexor hallucis brevis to electrical stimulation of the sacral nerve.

An exemplary electromyography measurement depicting a compound muscle action potential response in the flexor hallucis brevis to electrical stimulation of the sacral nerve is shown in FIG. 6. The electromyography measurement can be used to evaluate the placement and programming of a sacral nerve stimulator. For example, electromyography measurements can be used to determine the charge injection threshold for an implantable or transcutaneous neuromodulator (i.e. the minimum stimulation needed to produce muscle response).

Electromyography measurements are also used in some procedures to ensure that electrical stimulation is reaching the target tissue (i.e. the sacral nerve). For example, the surgical procedure for an implantable sacral nerve stimulator can involve intraoperative stimulation to confirm adequate placement of the electrode lead. This can involve placement of a probe (e.g. a foramen needle) in an area innervated by the targeted nerve or near another implantation site higher up the spinal cord (for indirect sacral nerve stimulation). The probe is used to deliver electrical stimulation until a desired muscle response is observed (e.g. a compound muscle action potential response in the flexor hallucis brevis). A lead with multiple electrodes can then be inserted at approximately the same location as the probe with high probability that at least one electrode will be in a position suitable for stimulating the targeted nerve. In at least some embodiments, the neuromodulator can be used to deliver intraoperative stimulation to confirm placement of the lead.

Immediately after the spike of an action potential there is a refractory period when the neuron is either unexcitable (absolute refractory period) or only activated to sub-maximal responses by supra-threshold stimuli (relative refractory period). The absolute refractory period occurs at the time of maximal Sodium channel inactivation. The relative refractory period occurs at a later time when most of the sodium ion (Na+) channels have returned to their resting state by the voltage activated potassium ion (K+) current. The refractory period has two important implications for action potential generation and conduction. First, action potentials can be conducted only in one direction, away from the site of its generation, and secondly, they can be generated only up to certain limiting frequencies.

Figure 7:
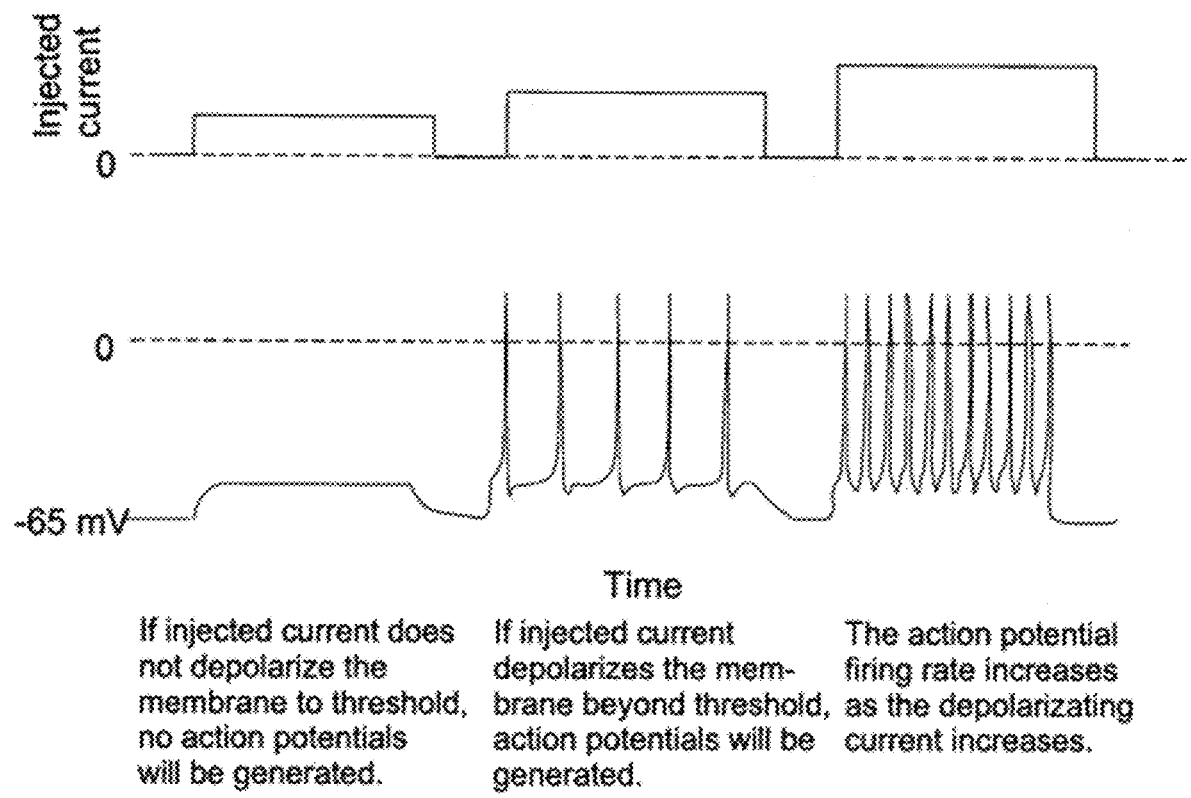
FIG. 7 is a schematic representation showing the response of the nervous system to different stimulation pulses.

The information in the nervous system is coded by frequency of firing rather than the size of the individual action potentials. The rate of action potential generation depends on the magnitude of the depolarizing current. That is, the firing frequency of action potentials reflects the magnitude of the depolarizing current. Although firing frequency increases with the amount of depolarizing current, there is a limit to the rate at which neurons can generate action potentials, depending on the absolute refractory period and the relative refractory period. The response of the nervous system to different stimulation pulses is shown schematically in FIG. 7.

The neural supply to the anorectal region is both somatic and autonomic. The superficial perineal nerve (branch of pudendal nerve) provides sensory fibres to the perineum, external genitalia as well as anal canal mucosa. Motor nerve supply to the pelvic floor and external anal sphincter is from the sacral plexus (S2-S4 level). The levator ani and puborectalis muscles are supplied on both the pelvic and perineal surfaces by direct branches from the nerve roots. The external anal sphincter receives its motor supply from the inferior rectal nerve (a branch of the pudendal nerve) and the deep perineal nerve (also a branch of the pudendal nerve) supplies the transverse perineal muscle and urethral sphincter.

The autonomic nerve supply is from both the sympathetic and parasympathetic systems. The sympathetic system is mainly inhibitory to colonic motility and excitatory to the internal anal sphincter. The supply is from the L1-L2 level via the hypogastric nerves. The parasympathetic supply is distributed via the sacral nerves (S2-S4) via the pelvic plexus and is excitatory to colonic motility as well as inhibitory to the internal anal sphincter. There is also an intrinsic nervous system of the colon and rectum with cell bodies within the colonic wall, but these can be affected by the autonomic system and local factors.

There appears to be a dual peripheral nerve supply (branches of the pudendal nerve and direct branches of sacral nerves) to the continence mechanism and the sacral spinal nerve is the most distal common location of this dual supply. Stimulation at this level can excite both nerves. Sacral nerve stimulation can be effective in those with large external sphincter defects, indicating that the treatment does not act solely at the sphincter level, but can recruit additional residual function of an inadequate pelvic floor musculature and pelvic organs.

Sacral nerve stimulation can alter colonic motility and/or remediate abnormal colonic motility. In at least some instances, sacral nerve stimulation can treat several colonic conditions, including chronic constipation, faecal incontinence, postoperative ileus, and colonic pseudo-obstruction. These diseases can share similar features, but they have distinct underlying mechanisms, which can complicate their clinical diagnosis. For example, in patients with faecal incontinence, sacral nerve stimulation can alter the colonic motor patterns involved in the rectosigmoid brake by increasing the number of retrograde propagating sequences. In at least some embodiments, the motor patterns produced in the colon in response to electrical stimulation of the sacral nerve can be used to evaluate the treatment efficacy of a neurostimulator. This is in contrast to electrically evoked compound action potential measurements that are sufficient to show electrical stimulation of the nerve (i.e. indicative that the nerve is firing). Conventional compound action potential measurements do not give an indication that the applied electrical stimulation is adequate to treat an underlying condition.

In at least some embodiments, colonic motor patterns can be used to set and/or adjust the stimulation parameters of the neuromodulator to achieve adequate treatment of faecal incontinence. For example, the pulse frequency, pulse width, pulse amplitude and/or pulse duration of the neuromodulator can be adjusted to achieve sustained cyclic retrograde propagating sequences in the lower descending colon and/or the rectosigmoid. In at least some embodiments, colon motility patterns can be measured non-invasively with a transcutaneous electrode array. In other embodiments, a subcutaneous electrode array (e.g. positioned in a pocket under the skin) can be used to measure colon motility patterns. The electrical stimulation delivered by the neuromodulator can be adjusted until the measured colon motility patterns are indicative of adequate treatment. For example, the charge injected by an implanted sacral nerve stimulator can be progressively raised using an external programmer (e.g. by changing the duration of the stimulation pulses) until retrograde propagating sequences with a frequency between 2 cycles per minute and 6 cycles per minute are measured. A transcutaneous electrode array can be used to measure colon motility and determine the threshold stimulation level needed to treat an underlying disorder (e.g. produce a rectosigmoid brake for patients suffering from faecal incontinence).

The charge delivered by an implantable sacral nerve stimulator to stimulate the sacral nerve can be adjusted responsive to measured colon motility patterns. The stimulation can be adjusted to produce rhythmic retrograde motor events occurring at about 2 to about 6 cycles per minute in the rectosigmoid. In some embodiments, the compliance voltage of the implantable sacral nerve stimulator can be set responsive to measured colon motility patterns. For example, the compliance voltage can be set based on the stimulation threshold needed to produce adequate motility patterns (e.g. with adequate headroom for the neuromodulator to remain in compliance). The response of smooth muscle in the colon to electrical stimulation of the spinal cord and/or sacral nerve can be measured transcutaneously. In some embodiments, the electrical activity in the recipient's colon can be measured transcutaneously and resolved into electrical waves that represent propagating contractions of smooth muscle within the colon. The propagation of the electrical waves along the recipient's colon can be spatially mapped responsive to the electrical stimulus delivered by the neuromodulator. In some embodiments, transcutaneous measurements are obtained by performing transcutaneous electrocolonography concurrent with electrical stimulation of the spinal cord or sacral nerve.

Colon activity can be measured for a period immediately after ingestion of a meal. For example, colon activity can be measured for a period of 40-60 minutes after meal ingestion when elevated rectosigmoid activity is expected. In some embodiments, the meal can be standardised to evoke a suitable colonic response. For example, the calorific content and fat/carbohydrate/protein/composition of the meal administered to patients can be standardised. Post meal electrocolonography measurements can be used to programme a sacral nerve stimulator to treat faecal incontinence. In some embodiments, the sacral nerve stimulator can be programmed to produce sustained of rhythmic retrograde motor events in the rectosigmoid. In at least some patients, the retrograde activity can act as a functional rectosigmoid brake that controls the flow of content into the rectum and/or reduces rectal filling.

A method for adapting the electrical stimulation delivered to the recipient of a sacral nerve stimulator responsive to the measured smooth muscle response is disclosed. The method comprises transcutaneously measuring the smooth muscle response of the colon to electrical stimulation of the spinal cord or sacral nerve and adapting the electrical stimulation responsive to the measured smooth muscle response. In some embodiments, the method can comprise resolving the electrical activity into electrical waves that each represent a propagating contraction of smooth muscle within the colon, and identifying colon dysmotility from the propagating electrical waves. The identified dysmotility can be used to adjust the charge delivered to the spinal cord or sacral nerve to treat the identified dysmotility. For example, the threshold for adequate stimulation can be identified by reducing the stimulation level (e.g. the charge delivered to the recipient's tissue) until the onset of dysmotility is detected.

In some patients, after colorectal surgery the distal colon can become hyperactive with excessive cyclic motor activities. This can act as a functional obstruction, slowing down gut recovery after some interventions (such as right hemicolectomy). The hyperactivity can be caused by excessive sympathetic activation, arising as a stress response to surgery. In this case, stimulation of the sacral nerves, which are parasympathetic, can increase parasympathetic outflow. The increased parasympathetic outflow can provide a counterbalance to the excessive sympathetic activity, returning colonic motility towards normal. These changes can be detected using a transcutaneous electrode array that is placed over the distal colon or rectosigmoid region after surgery. The measurements obtained from the array can be used to control an electrical stimulus delivered to the sacral nerves (e.g. the parameters of neuromodulator).

In some embodiments, the level of electrical stimulation delivered to the patient is progressively reduced until the smooth muscle response of the colon is indicative of a colonic motility disorder. The level of electrical stimulation (e.g. the frequency, width, amplitude and/or duration of electrical pulses delivered to tissue) can then be progressively increased to induce retrograde propagating sequences in the colon. For example, the stimulation delivered by the implantable sacral nerve stimulator can be increased to a sufficient level to produce a rectosigmod brake in the lower descending colon and/or in the rectosigmoid following ingestion of a meal.

A method of delivering electrical stimulation to a patient to treat a colonic motility disorder is disclosed. The method comprises measuring propagating electrical activity in the colon of the patient, responsive to electrical stimulation, with an electrode matrix positioned on the abdomen of the patient, and modifying the electrical stimulation delivered to the patient in order to evoke an altered motility pattern in the colon. The electrode matrix is adhered to the skin of the patient overlying a rectosigmoid segment of the colon. In some embodiments, the electrode matrix is centred over a section of the abdomen between the left iliac crest and the midline of the patient. For some patients, the electrode matrix can be centred over a section of the abdomen between the umbilicus and an upper region of the symphysis pubis. The method can comprise measuring post meal activity in the lower descending colon and/or rectosigmoid, and modifying the electrical stimulation to produce a motility pattern that reduces the incidence of faecal incontinence. In some embodiments, the method comprises modifying the electrical stimulation to modify a measured motility pattern. For example to produce a rectosigmoid brake or a cyclic motor patterns.

Figure 8:
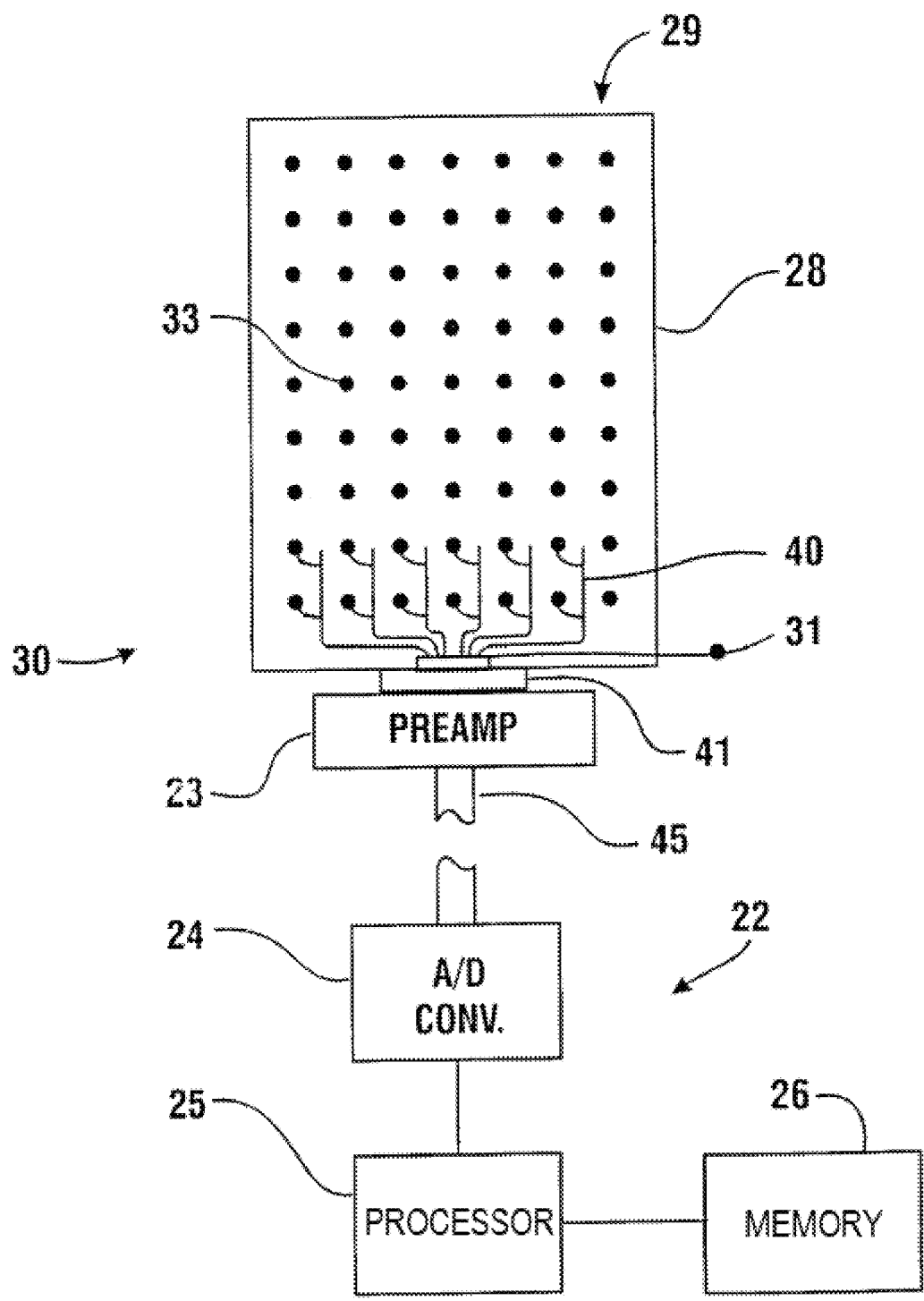
FIG. 8 is a schematic representation of a wearable transcutaneous electrocolonography system.

A wearable transcutaneous electrocolonography (EColG) system 30 is shown schematically in FIG. 8. The body worn system 30 is configured to noninvasively measure electrical slow wave propagation in the colon form the body surface. The measurements represent colonic motility. The illustrated body worn system 30 comprises a multichannel electrode array 29 that is configured to obtain skin-surface electrical recordings from the lower abdominal region of a recipient. The electrode array illustrated in FIG. 8 comprises a compliant fabric substrate 28 that conforms to the recipient's torso. The substrate 28 supports a matrix of electrodes 33 and electrical traces 40. The electrodes 33 can be integral with the substrate 28 (e.g. a flex PCB with printed electrodes) or secured to the substrate 28 (e.g. a belt with electrodes fastened or adhered to the fabric). In some embodiments, the electrode array 29 comprises a plurality of individual electrodes that are adhered to the skin in a matrix configuration (i.e. the recipient's skin holds the electrodes in an array). An exemplary electrode array 29 comprising individual sensing electrodes adhered to the skin of a recipient is shown in FIG. 9 (the reference electrodes are not shown).

Figure 9:
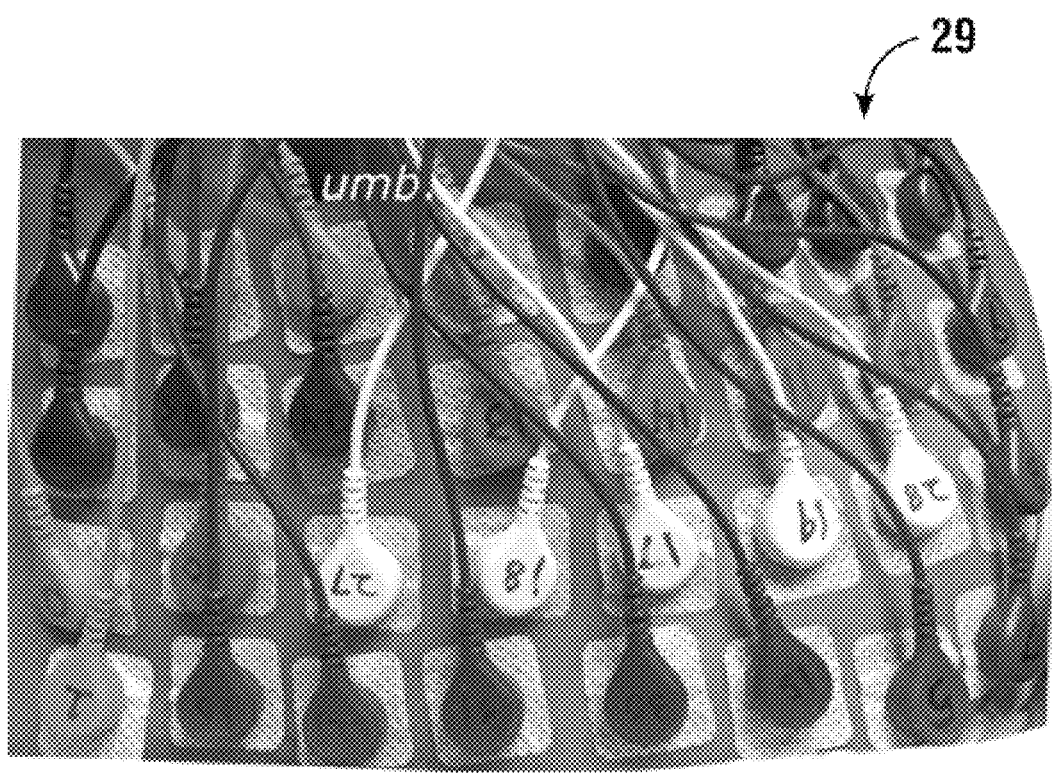
FIG. 9 is an image of a transcutaneous electrocolonography electrode array that comprises individual sensing electrodes adhered to the skin of a recipient
Figure 10:
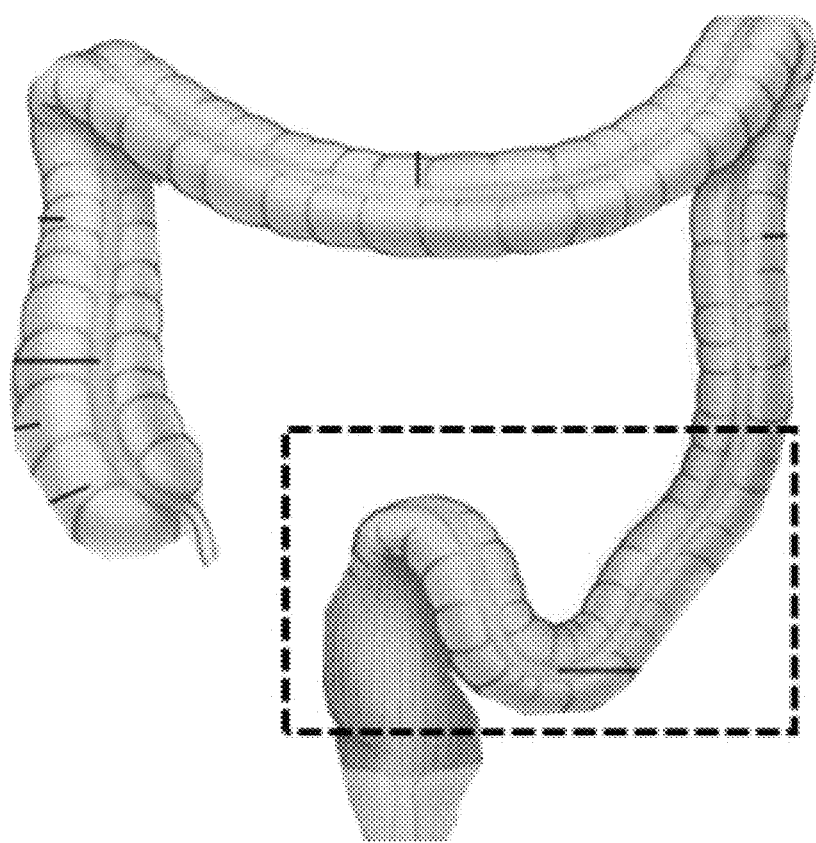
FIG. 10 is a schematic representation of a human colon showing the approximate position of the lower descending and rectosigmoid segments.

The electrodes 33 shown in FIG. 9 are adhered to the skin in the lower abdominal region of a recipient. The depicted electrodes 33 are positioned over a section of the abdomen that is horizontally bounded by the left iliac crest and the midline of the patient, and vertically bounded by the umbilicus and an upper region of the symphysis pubis. In some embodiments, the electrode array 29 can be positioned further to the recipient's left side and/or extend above the umbilical line (e.g. near the epigastric region) in order to better target descending and sigmoid colon activity. In other embodiments, the top of the electrode array 29 can be placed level with or below the umbilicus, and span the recipient's midline in order to target rectosigmoid activity. The dashed box shown in FIG. 10 indicates the approximate position of an electrode array 29 covering the lower descending and rectosigmoid segments of the colon. The reference electrode(s) are placed away from electrode array 29 (e.g. on or near the right iliac crest).

The electrode array 29 is configured to produce high-resolution colonic electrograms. A high resolution colonic electrode array comprises at least 16 electrodes (excluding reference electrodes). An ultra-high resolution colonic electrode array comprises at least 24 electrodes (excluding reference electrodes). In some embodiments, the electrode array comprises between 24 and 36 electrodes. The electrode array 29 depicted in FIG. 9 comprises 32 sensing electrodes. The electrode array 29 depicted in FIG. 8 comprises 61 sensing electrodes and a single reference electrode 31. The reference electrodes are not shown in FIG. 9. Each of the sensing electrodes 33 measures a localised change in electrical potential adjacent the skin surface. The change in electrical potential is measured relative to a reference electrode. Each of the electrodes is electrically connected to a conductor (e.g. traces 40). The conductors carry electrical signals (e.g. electrical potentials) between the electrodes 33 and a connector 41 disposed at the base of the electrode array 29.

The multichannel output from the electrode array 29 (i.e. the electrical signals measured by each of the electrodes 33) is fed into an amplifier 23. The amplifier 23 is secured to the base of the electrode array 29 in the illustrated embodiment. It boosts the electrical signal on each channel before transmission to the body worn electronics 22. A cable 45 electrically connects the amplifier 23 to the body worn electronics 22. The body worn electronics 22 process (e.g. timestamp, filter, normalise) and store the electrical signals obtained by the electrode array 29. The illustrated electronics 22 comprise an analogue-to-digital converter 24, a digital processor 25 (e.g. an ASIC or microcontroller) and non-volatile memory 26.

The data stored in the body worn electronics 22 can be transferred to a centralised (e.g. non-worn) system for more resource intensive processing. For example, data stored in the non-volatile memory 26 can be downloaded to a clinical processor (such as a device programmer) and uploaded to a cloud system. The cloud system can process the measurements obtained from the transcutaneous electrode array 29 to isolate components corresponding to colonic electrophysiological activity. In some embodiments, the centralised system can be configured to quantify the spectral power in the colonic frequency band (2-6 cycles per minute). For example, a signal processing pipeline based on Continuous Wavelet Transform (CWT) time-frequency analysis can be used for spectral power analysis. The electrocolonography recordings obtained from the body worn system 30 can be used to quantify the recipient's meal-response (i.e. the motility patterns produced in the lower descending colon and/or rectosigmoid in response to meal ingestion).

In some embodiments, the signal processing pipeline can comprise baseline drift correction, movement artefact reduction and/or band-pass filtering. For example, a moving median can be used to correct low frequency artifacts or drift (e.g. less than 0.02 Hz) that are caused by the time-varying impedance of the electrode skin interface. In at least some embodiments, the changes in baseline can be reduced by subtracting a moving median with a 10 s half-window. Some forms of movement artifact (e.g. motion and other large transient artifacts) can be alleviated with Linear Minimum Mean Square Error processing. For example, relatively large amplitude, short time-scale artifacts can be identified and subtracted in regions where the time-local variance of the recorded signal is much greater than the variance of the underlying colonic component. Bandpass filtering can be used to isolate colonic motor patterns from out-of-band interference (such as electrical activity attributable to cardiac function and/or respiration). For example, a bandpass frequency range of 0.5-10 cycles per minute can be used to remove signal components outside the typical range for colonic motor patterns.

Figure 11:
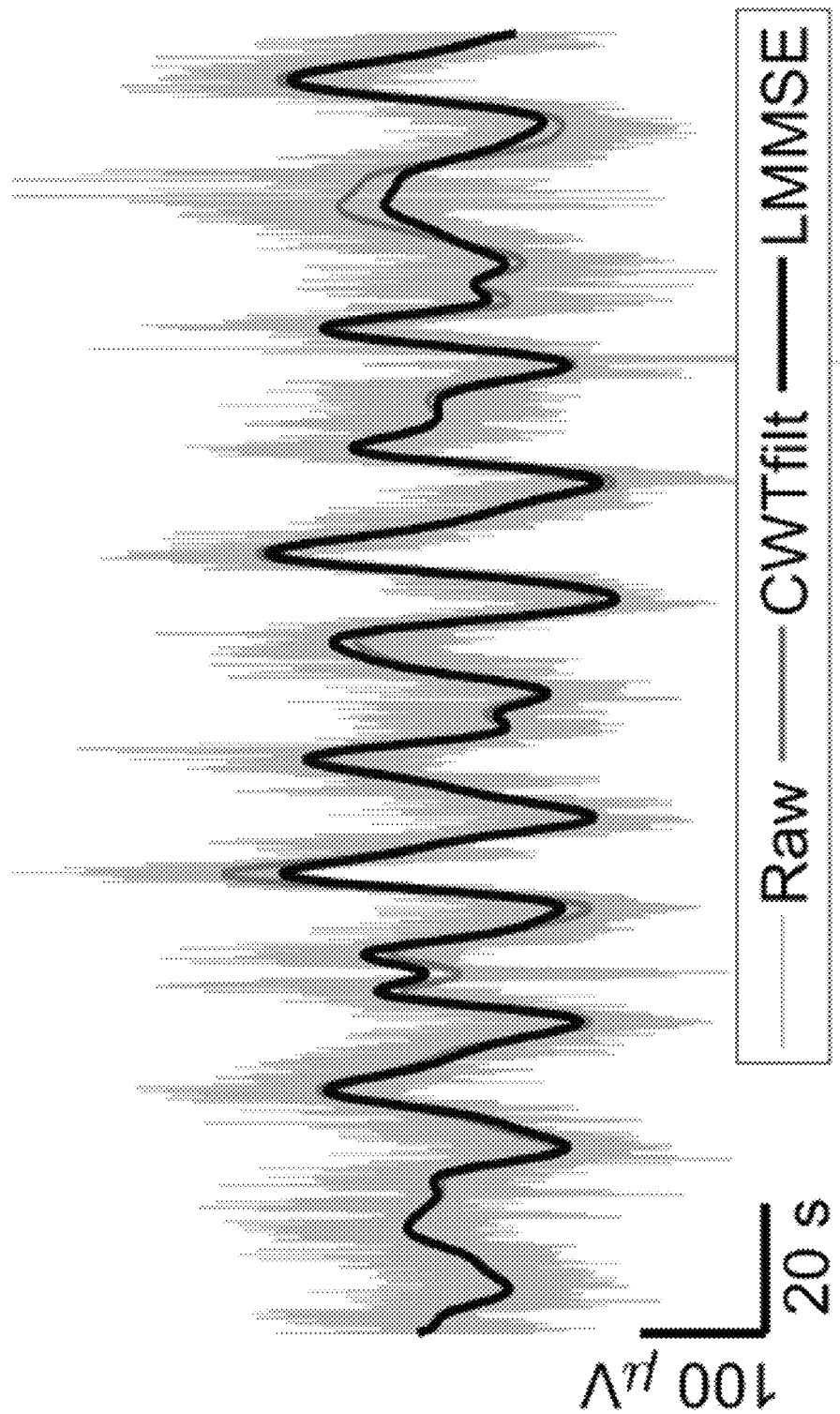
FIG. 11 is a graphical representation that shows the application of a Continuous Wavelet Transform and Linear Minimum Mean Square Error artefact reduction to a raw electrocolonography signal.

An electrocolonography signal is shown in FIG. 11. The raw signal is processed using Linear Minimum Mean Square Error artefact reduction with a 20 s window that approximately averages over one period of oscillation of the colonic component. A band pass filter (0.5-10 Hz) is then applied by hard thresholding of out-of-band Continuous Wavelet Transform coefficients. The periodicity of approximately 20 s in the depicted signal is indicative of colonic motor activity at approximately 3 cycles per minute. Activity in the colon can be localised with body surface intensity mapping. For example, the regions of the colon that become active during a post-meal period can be identified by mapping a power percent difference for each of the individual electrodes 33 comprising the electrode array 29. The electrodes 33 that have a high power percent difference value correspond to active segments of the colon. For example, the rectosigmoid and sigmoid to descending segments of the colon can become strongly activated post-meal. This activity can become evident in the infr-aumbilical region in body surface intensity maps.

Any method detailed herein also corresponds to a disclosure of a device and/or system configured to execute one, or more, or all, of the method actions. Likewise, any disclosure of a device and/or system detailed herein corresponds to a method of making and/or using the device and/or system, including a method of using that device according to the functionality detailed herein. And any disclosure of a device and/or system detailed herein also corresponds to a disclosure of otherwise providing that device and/or system.

In at least some exemplary embodiments, any feature disclosed herein can be utilized in combination with any other feature disclosed herein unless otherwise specified. Accordingly, exemplary embodiments include a medical device including one or more or all of the teachings detailed herein, in any combination. While various embodiments have been described, they have been presented by way of example only, and not limitation. Changes in form and/or detail can be made therein without departing from the invention.

The invention claimed is:

1. A method comprising transcutaneously measuring motility patterns, in the colon of a recipient of an implantable neuromodulator, responsive to an electrical stimulus delivered by the implantable neuromodulator, and programming the implantable neuromodulator responsive to the measured motility patterns, wherein the method comprises adjusting at least one parameter of the implantable neuromodulator that defines the electrical stimulus that the implantable neuromodulator is configured to deliver to the recipient, wherein the method comprises transcutaneously measuring the response of smooth muscle in the colon to electrical stimulation of the spinal cord or the sacral nerve.

2. The method of claim 1, wherein the method comprises setting the charge that the implantable neuromodulator is configured to deliver to stimulate the sacral nerve or spinal cord of the recipient responsive to the measured colon motility patterns.

3. The method of claim 1, wherein the method comprises setting a compliance voltage for the implantable neuromodulator responsive to the measured colon motility patterns.

4. The method of claim 1, wherein the method comprises setting at least one of a pulse width, a pulse amplitude, or a pulse frequency for the electrical stimulus that the implantable neuromodulator is configured to deliver to the recipient.

5. The method of claim 1, wherein the method comprises the implantable neuromodulator stimulating the spinal cord or sacral nerve of the recipient, with an electrical stimulus defined by the at least one adjusted parameter, and measuring the motility patterns, in the colon of the recipient, responsive to the electrical stimulus.

6. The method of claim 1, wherein the method comprises adjusting the at least one parameter of the electrical stimulus that the implantable neuromodulator is configured to deliver to the recipient until the measured motility patterns are indicative of rhythmic retrograde motor events occurring at about 2 to about 6 cycles per minute in the rectosigmoid.

7. The method of claim 1, wherein the method comprises adjusting the at least one parameter of the electrical stimulus that the implantable neuromodulator is configured to deliver to the recipient until the measured motility patterns are indicative of a rectosigmoid brake or cyclic motor pattern in the lower descending colon and/or in the rectosigmoid following ingestion of a meal.

8. The method of claim 1, wherein the method comprises transcutaneously measuring the electrical activity of the recipient's colon, and resolving the electrical activity into electrical waves that are indicative of colonic motility, wherein each electrical wave represents a propagating contraction of smooth muscle within the colon.

9. The method of claim 8, wherein the method comprises spatially mapping the propagation of the electrical waves along the recipient's colon responsive to electrical stimulation of the spinal cord or sacral nerve.

10. The method of claim 1, wherein the method comprises performing transcutaneous electrocolonography concurrently with electrical stimulation of the spinal cord or sacral nerve.

11. A method comprising transcutaneously measuring a smooth muscle response, in the colon of a patient, to electrical stimulation of the spinal cord or the sacral nerve, and adapting at least one characteristic of the electrical stimulation delivered to the spinal cord or the sacral nerve responsive to the measured smooth muscle response, wherein the method comprises identifying colonic dysmotility from the propagating electrical waves, and adjusting the charge delivered to the spinal cord or the sacral nerve to treat the identified dysmotility.

12. The method of claim 11, wherein the method comprises transcutaneously measuring electrical activity of the patient's colon, and resolving the electrical activity into electrical waves that are indicative of colonic motility, wherein each electrical wave represents a propagating contraction of smooth muscle within the colon.

13. The method of claim 12, wherein the method comprises progressively increasing the current delivered to the spinal cord or sacral nerve of the patient to induce retrograde propagating sequences in the colon.

14. The method of claim 11, wherein the method comprises progressively reducing the current delivered to the patient until the smooth muscle response of the colon is indicative of a colonic motility disorder.

15. A method comprising delivering electrical stimulation to a patient to treat a colonic motility disorder, wherein the method comprises measuring propagating electrical activity in the colon of the patient, responsive to the electrical stimulation, with an electrode matrix positioned on the abdomen of the patient, and modifying the electrical stimulation delivered to the patient in order to evoke an altered motility pattern in the colon.

16. The method of claim 15, wherein the method comprises centering the electrode matrix over a section of the abdomen between the left iliac crest and the midline of the patient.

17. The method of claim 15, wherein the method comprises centering the electrode matrix over a section of the abdomen between the umbilicus and an upper region of the symphysis pubis.

18. The method of claim 15, wherein the method comprises adhering the electrode matrix to the skin of the patient overlying a rectosigmoid segment of the colon.

19. The method of claim 15, wherein the method comprises measuring post meal activity in the lower descending colon and/or rectosigmoid, and modifying the electrical stimulation to produce a motility pattern that reduces the incidence of faecal incontinence.

20. The method of claim 15, wherein the method comprises modifying the electrical stimulation to produce a rectosigmoid brake or cyclic motor patterns.

* * * * *